US00PP21113P2

(12) United States Plant Patent

Klemm et al.

(10) Patent No.: US PP21,113 P2

(45) Date of Patent: Jun. 29, 2010

(54) *PELARGONIUM* PLANT NAMED 'KLEPZ08231'

(50) Latin Name: *Pelargonium zonale*
Varietal Denomination: KLEPZ08231

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,554

(22) Filed: Mar. 25, 2009

(51) Int. Cl.
*A01H 5/00* (2006.01)

(52) U.S. Cl. ..... Plt./329

(58) Field of Classification Search ..... Plt./329
See application file for complete search history.

*Primary Examiner*—Susan B McCormick Ewoldt
(74) *Attorney, Agent, or Firm*—Jondle & Associates, P.C.

(57) ABSTRACT

A new cultivar of *Pelargonium* named 'KLEPZ08231' particularly characterized by shiny purple-pink inflorescences, a medium to strong and harmonic growth habit, and produces a large number of cuttings for propagation, is disclosed.

1 Drawing Sheet

Genus and species: *Pelargonium zonale.*
Variety denomination: 'KLEPZ08231'.

BACKGROUND OF THE NEW PLANT

The present invention comprises a new and distinct cultivar of *Pelargonium*, botanically known as *Pelargonium zonale*, and hereinafter referred to by the cultivar name 'KLEPZ08231'. 'KLEPZ08231' was discovered as a seedling resulting from a controlled cross in May 2004 in Stuttgart, Germany between the proprietary female *Pelargonium* parent, 'Z 21057' (unpatented) and the proprietary male *Pelargonium* parent, 'KLEP01012' (U.S. Plant Pat. No. 13,743). A single plant selection was subsequently chosen for further evaluation and for asexual propagation.

The new cultivar was created in 2004 and first propagated in August 2005 in Stuttgart, Germany and has been asexually reproduced repeatedly by vegetative cuttings in Stuttgart, Germany over a three and one-half year period. 'KLEPZ08231' has been found to retain its distinctive characteristics through successive asexual propagations.

Plant Breeder's Rights for this cultivar were applied for in Switzerland on Jun. 19, 2008 and in Canada on Mar. 28, 2008. 'KLEPZ08231' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Shiny purple-pink inflorescences;
2. A medium to strong and harmonic growth habit; and
3. Produces a large number of cuttings for propagation.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures. The photograph is of a three-month old plant taken in Spring 2008 and grown from rooted cuttings in a 12-cm pot in a greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPZ08231'. The data which define these characteristics were collected from asexual reproductions carried out in Stuttgart, Germany. The plant history was taken on three-month old, un-pinched plants in 12-cm pots in a greenhouse in January through April. The color readings were determined under natural light. Color references are to The R.H.S. Colour Chart of The Royal Horticultural Society of London (R.H.S.) (2001).

DETAILED BOTANICAL DESCRIPTION

Classification:

*Family.*—Geraniacaea.
*Species.*—*Pelargonium zonale.*
*Common name.*—*Pelargonium* (Geranium).
*Denomination.*—'KLEPZ08231'.

Parentage:

*Female parent.*—The proprietary female *Pelargonium* parent, 'Z 21057' (unpatented).
*Male parent.*—The proprietary male *Pelargonium* parent, 'KLEP01012' (U.S. Plant Pat. No. 13,743).

Plant:

*Habit.*—Upright.
*Height.*—16.0 cm.
*Spread.*—28.0 cm.
*Life cycle.*—Spring to autumn.
*Form.*—Rounded, bushy.
*Time to produce a rooted cutting.*—18 days.
*Time to bloom from propagation.*—Approximately 76 days.
*Flowering requirements.*—No.
*Lastingness of inflorescence on the plant.*—10 to 14 days.

Stems:
*Stem color.*—RHS 137C.
*Pubescence.*—Weak, short.
*Pubescence color.*—Greenish white.
*Stem form.*—Round.
*Diameter.*—0.8 cm to 1.0 cm.
*Length.*—8.0 cm to 10.0 cm.
*Internode length.*—0.8 cm to 2.0 cm.

Leaves:
*Arrangement.*—Alternate.
*Shape.*—Transverse elliptical.
*Apex.*—Round.
*Base.*—More open.
*Margin.*—Entire.
*Surface texture.*—Upper surface: Smooth. Lower surface: Dull.
*Length.*—4.0 cm to 6.0 cm.
*Width.*—4.0 cm to 7.0 cm.
*Color.*—Upper surface: RHS 139A. Lower surface: RHS 137B.
*Surface pubescence.*—Pubescent, with extremely short hairs.
*Petiole.*—Length: 2.0 cm to 10.0 cm. Color: RHS 137B.
*Venation pattern.*—Palmate.
*Venation color.*—RHS 137C.

Inflorescence:
*Flowering habit.*—Continuous.
*Umbels.*—Length: 6.0 cm to 8.0 cm. Diameter: 10.0 cm to 12.0 cm.
*Individual florets of the umbel.*—Depth: 1.5 cm. Diameter: 4.5 cm.
*Fragrance.*—Absent.

Flower buds:
*Cluster shape.*—Round-ovate.
*Length.*—1.0 cm to 3.0 cm.
*Width.*—1.0 cm to 4.0 cm.
*Texture.*—Smooth (not pubescent).
*Bud.*—Shape: Elliptic, shell-shaped. Apex: Acute. Base: Blunt, truncated. Margin: Entire, smooth. Color: RHS 137B. Size: Length: 1.0 cm to 1.4 cm. Width: 0.5 cm to 0.8 cm.

Petals:
*Quantity per flower.*—5 to 8.
*Shape.*—Drop-shaped, elliptic.
*Apex.*—Round.
*Base.*—Obtuse.
*Margin.*—Entire.
*Length.*—3.0 cm.
*Width.*—2.5 cm.
*Color of lobes.*—Upper lobes (both surfaces): RHS N57A. Lower lobes (both surfaces): RHS 73C.
*Fragrance.*—Absent.

Sepals:
*Number per flower.*—5.
*Shape.*—Lanceolate.
*Apex.*—Acute.
*Base.*—Obtuse.
*Margin.*—Entire.
*Color (both surfaces).*—RHS 137B and RHS 138B.
*Length.*—1.4 cm.
*Width.*—0.3 cm to 0.4 cm.

Pedicel:
*Length.*—2.5 cm to 3.5 cm.
*Diameter.*—0.15 cm.
*Color.*—RHS 185A.

Peduncle:
*Length.*—14.0 cm to 18.0 cm.
*Diameter.*—0.4 cm.
*Color.*—RHS 176A to RHS 176C and RHS 137C.
*Texture.*—Rough.

Reproductive organs:
*Stamens.*—Anther length: 0.2 cm. Filament length: 0.5 cm to 0.7 cm. Filament color: RHS 45D and RHS 66D. Pollen amount: Moderate. Pollen color: RHS 32A.
*Pistils.*—Number: 1. Stigma color: RHS 64B. Style length: Small. Style color: RHS 137D. Ovary arrangement: Central, middle.

Fruit/seed set: None observed.

Disease and insect resistance: No particular disease or insect resistance observed.

COMPARISON WITH PARENTAL AND COMMERCIAL CULTIVARS

'KLEPZ08231' differs from the female parent, the proprietary female *Pelargonium* parent, 'Z 21057' (unpatented) in that 'KLEPZ08231' has a purple-pink flower color and medium to strong growth habit, while 'Z 21057' has a blue-pink flower color and a strong growth habit.

'KLEPZ08231' differs from the male parent, the proprietary male *Pelargonium* parent, 'KLEP01012' (U.S. Plant Pat. No. 13,743) in that 'KLEPZ08231' has a purple-pink flower color (RHS 57A), while 'KLEP01012' has a dark pink flower color (RHS 66A). In addition, 'KLEPZ08231' has longer and wider petals than 'KLEP01012'.

'KLEPZ08231' differs from the commercial comparison variety 'Fisum Pink' (U.S. Plant Pat. No. 16,101) in that 'KLEPZ08231' has a purple-pink flower color and a dark green leaf color, while 'Fisum Pink' has a salmon-pink flower color and a light green leaf color.

I claim:

1. A new and distinct cultivar of *Pelargonium* plant named 'KLEPZ08231' as shown and described herein.

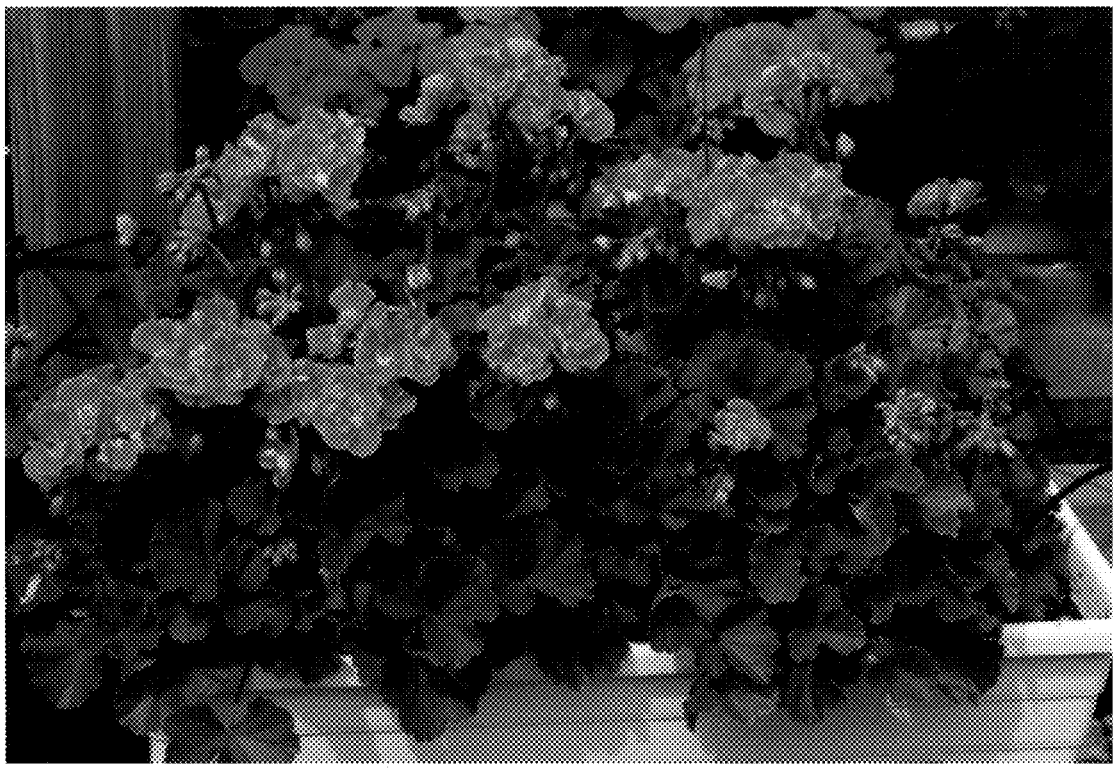

* * * * *